United States Patent
Ray et al.

(10) Patent No.: US 9,612,210 B2
(45) Date of Patent: Apr. 4, 2017

(54) SYSTEMS AND METHODS FOR AUTOMATICALLY INSPECTING WIRE SEGMENTS

(71) Applicant: THE BOEING COMPANY, Huntington Beach, CA (US)

(72) Inventors: Gary Alan Ray, Issaquah, WA (US); Bentley Edwin Northon, Auburn, WA (US); Bradley J. Mitchell, Snohomish, WA (US); James Ridgeway Gillis, Seattle, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 14/750,447

(22) Filed: Jun. 25, 2015

(65) Prior Publication Data

US 2016/0377555 A1  Dec. 29, 2016

(51) Int. Cl.
*G01N 21/00* (2006.01)
*G01N 21/952* (2006.01)
*G01N 21/88* (2006.01)
*H01R 43/05* (2006.01)

(52) U.S. Cl.
CPC ....... *G01N 21/952* (2013.01); *G01N 21/8806* (2013.01); *H01R 43/05* (2013.01); *G01N 2021/8848* (2013.01)

(58) Field of Classification Search
CPC ...... G01N 21/00; G01N 2201/00; G06T 7/00; G01B 11/00
USPC ........................................... 356/237.2–237.6
See application file for complete search history.

(56) References Cited

U.S. PATENT DOCUMENTS

| | | | | |
|---|---|---|---|---|
| 3,761,182 A * | 9/1973 | Kubisiak | .................. | B07C 5/10 |
| | | | | 250/559.22 |
| 5,050,093 A | 9/1991 | Reddy et al. | | |
| 5,383,022 A * | 1/1995 | Kaser | .................... | G01B 11/02 |
| | | | | 250/559.19 |
| 6,072,575 A | 6/2000 | Loell | | |
| 6,842,258 B1 | 1/2005 | Leinvuo et al. | | |
| 8,331,648 B2 * | 12/2012 | Keeven | .................... | H01R 4/22 |
| | | | | 356/237.1 |
| 2003/0007793 A1 * | 1/2003 | Suzuki | ................... | G03B 37/02 |
| | | | | 396/20 |
| 2004/0207818 A1 * | 10/2004 | Stahl | .................... | G03B 21/142 |
| | | | | 353/38 |
| 2008/0100928 A1 * | 5/2008 | Wilson | .................. | A61B 1/041 |
| | | | | 359/725 |

(Continued)

OTHER PUBLICATIONS

EP Extended Search Report for related application 16175756.2 dated Oct. 27, 2016; 7 pp.

*Primary Examiner* — Tarifur Chowdhury
*Assistant Examiner* — Isiaka Akanbi
(74) *Attorney, Agent, or Firm* — Armstrong Teasdale LLP

(57) ABSTRACT

A wire inspection system is provided. The wire inspection system includes a mirror assembly including an odd number of sides arranged to form a pyramid structure configured to surround a wire segment, wherein a plurality of the sides include a mirror, a light source configured to illuminate the wire segment, and at least one camera configured to acquire a plurality of images of the wire segment that are reflected by the plurality of mirrors, wherein each image of the plurality of images shows a different side of the wire segment.

18 Claims, 19 Drawing Sheets

(56) References Cited

U.S. PATENT DOCUMENTS

| | | | |
|---|---|---|---|
| 2008/0266523 A1* | 10/2008 | Otsuka | G02B 27/2285 353/7 |
| 2013/0063591 A1* | 3/2013 | Bainbridge | H01R 43/055 348/135 |
| 2014/0036260 A1* | 2/2014 | Nygaard | B07C 5/342 356/237.2 |

* cited by examiner

SYSTEMS AND METHODS FOR AUTOMATICALLY INSPECTING WIRE SEGMENTS

BACKGROUND

The field of the present disclosure relates generally to wire inspection techniques and, more specifically, to an apparatus and methods that facilitate efficient inspection of a wire segment.

Many modern technological assemblies include electrical wires that must undergo a series of processing steps prior to their installation within the assembly. More specifically, electrical wires are generally delivered in large spools, such that each portion of electrical wire is measured and cut, each end of the cut electrical wire is stripped and inserted into a specific end piece, and each end is crimped to facilitate sufficient electrical contact with a lug, pin, or socket, for example. Several errors may occur during one or more of these processing steps. For example, an insufficient amount of electrically conductive material may be exposed after the stripping step, or stray strands of electrically conductive material may be exposed if an end of the electrical wire is improperly inserted into a lug, pin, or socket. At least some of these electrical wires are visually inspected by a technician to ensure the electrical wire has been properly processed prior to its installation within the assembly. This inspection is a time-consuming and laborious task because the entire area about the processed portions of the electrical wire must be inspected carefully, and there is typically a large number of such wire segments to be inspected.

At least some known wire strip machines and automatic crimp machines have built-in inspection systems. However, these systems generally are able to only perform a single inspection operation (i.e., strip or crimp inspection) on a single type of wire.

BRIEF DESCRIPTION

In one aspect a wire inspection system is provided. The wire inspection system includes a mirror assembly including an odd number of sides arranged to form a pyramid structure configured to surround a wire segment, wherein a plurality of the sides include a mirror, a light source configured to illuminate the wire segment, and at least one camera configured to acquire a plurality of images of the wire segment that are reflected by the plurality of mirrors, wherein each image of the plurality of images shows a different side of the wire segment.

In another aspect an automated wire segment processing system is provided. The system includes a strip station configured to strip a wire segment, a crimp station configured to crimp the wire segment, a controller configured to control operation of the strip station and the crimp station, and a wire inspection system configured to assess at least one of a strip quality of a stripping operation performed on the wire segment by the strip station and a crimp quality of a crimping operation performed on the wire segment by the crimp station. The wire inspection system includes a mirror assembly including an odd number of sides arranged to form a pyramid structure configured to surround the wire segment, wherein a plurality of the sides include a mirror, a light source configured to illuminate the wire segment, and at least one camera configured to acquire a plurality of images of the wire segment that are reflected by the plurality of mirrors, wherein each image of the plurality of images shows a different side of the wire segment.

In yet another aspect a method for inspecting a wire segment is provided. The method includes inserting the wire segment into a mirror assembly, the mirror assembly including an odd number of sides arranged to form a pyramid structure that surrounds the wire segment, wherein a plurality of the sides include a mirror, illuminating the wire segment using a light source, acquiring a plurality of images of the wire segment that are reflected by the plurality of mirrors, wherein each image of the plurality of images shows a different side of the wire segment, and analyzing the plurality of images using a computing device to assess at least one of a strip quality and a crimp quality of the wire segment.

DETAILED DESCRIPTION

The systems and methods described herein facilitate automated inspection of wire segments for strip and crimp quality. The implementations described herein are not limited to use with wire inspection systems, but may also be used for other applications that involve optical inspection of objects from multiple directions. Further, the systems and methods described herein facilitate inspecting wire segments of multiple wire types, and can be integrated with existing wire strip and crimp machines.

The inspection systems described herein are fully automated, and are able to inspect multiple wire types using a relatively simple optical design. Further, unlike at least some known systems, to determine a wire type, the implementations described herein do not need to inspect wire labels using visual character recognition. The systems and methods described herein also overcome multiple mirror reflection issues and camera self-reflection issues associated with at least some known wire inspection systems. In one implementation, for example, five mirrors are used to create a five-sided view of the wire segment. Because it is unnecessary to view larger portions of the wire segment, smaller optics and a smaller focal plane may be used, while still capturing a comprehensive set of side views of the wire in one image frame. This facilitates reducing inspection and processing times.

Compared to human inspection, the automated inspection systems and methods described herein reduce operating costs, reduce eyestrain, and increase speed and accuracy. Compared to other known automated approaches, the implementations described herein enable a single inspection station to inspect a wide variety of wire segments with different types of wire and different contacts, reducing costs and improving reliability. In addition, the systems and methods described herein reduce operating footprints in facilities where many different types of wire segments are used. Further, with the optical design described herein, inspections inside a constrained inspection module area are supported. This facilitates eliminating imaging problems from outside light and internal unwanted reflections, and facilitates acquiring high contrast images with economical usage of relatively inexpensive digital microscopes, single machine vision, and/or electronic shutter single-lens reflex (SLR) high resolution cameras.

When implemented as a component of a planned automation system, the implementations described herein facilitate reducing labor costs, maintaining or improving quality, increasing inspection speed, and improving safety for producing wire segments and wire bundles. The systems described herein may be installed in-line in existing wire stripping and crimping machines for operation in real-time to quickly inspect (e.g., less than one second for the entire inspection process) and stop the stripping or crimping machine in the event of a detected defect.

Figure 1:
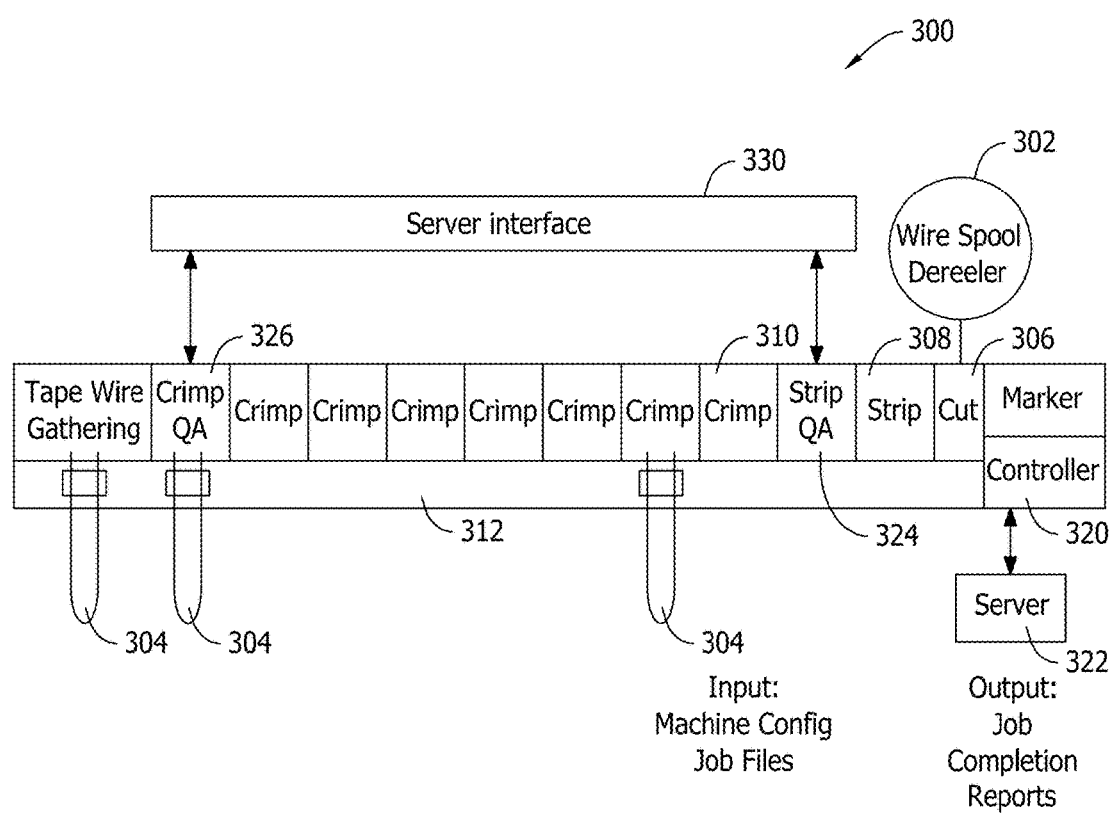
FIG. 1 is a schematic diagram of an exemplary automated wire segment processing system.

Environments such as aircraft, spacecraft, naval vessels, automobiles, power stations, operation control centers (e.g., for controlling fleets of aircraft, trains, electrical power networks, military units, etc.), and network routers contain thousands or even millions of wire segments. Both ends of each wire segment are electrically connected to some other component. Forming these connections is a process that includes many steps. The process may include cutting spools of wire into segments of appropriate length, stripping the insulation off of the ends of each cut segment to reveal the conductor, firmly attaching a contact (e.g., a lug, pin, or socket) to the bare conductor (e.g., by crimping), inserting the contacts into some type of connector, and plugging pairs of connectors together. Each step is subject to error, and if connections are incorrectly formed, the underlying product may not function properly. In existing systems, many of these steps are performed by a human technician. For example, for strip and crimp operations, the technician may visually inspect each wire segment. This is a labor intensive process that is relatively costly and time-consuming FIG. 1 is a schematic diagram of an exemplary automated wire segment processing system 300. A wire spool dereeler 302 unspools wire so the wire may be cut into wire segments 304 by a cutter 306. A strip station 308 strips the ends of each wire segment 304, and a crimp station 310 crimps end pieces onto each wire segment 304. To enable processing of different types of wire segments, system 300 may include multiple strip stations 308 and multiple crimp stations 310, with each strip station 308 and crimp station 310 programmed to perform a single type of stripping or crimping operation.

A wire transport system 312 moves wire segments 304 from one station to another. In the exemplary implementation, wire transport system 312 is controlled by a computer implemented controller 320. Controller 320 tracks the type of each wire segment 304 and controls wire transport system 312 to ensure each wire segment 304 is inserted into the appropriate strip station 308 and/or crimp station 310. Controller 320 is communicatively coupled to a server 322 in the exemplary implementation.

System 300 further includes a strip inspection station 324 and a crimp inspection station 326. Strip inspection station 324 inspects the result of each strip operation performed by strip stations 308. Similarly, crimp inspection station 326 inspects the result of each crimp operation performed by crimp stations 310. Strip and crimp inspection stations 324 and 326 are communicatively coupled to a server interface 330 of server 322.

Figure 2:
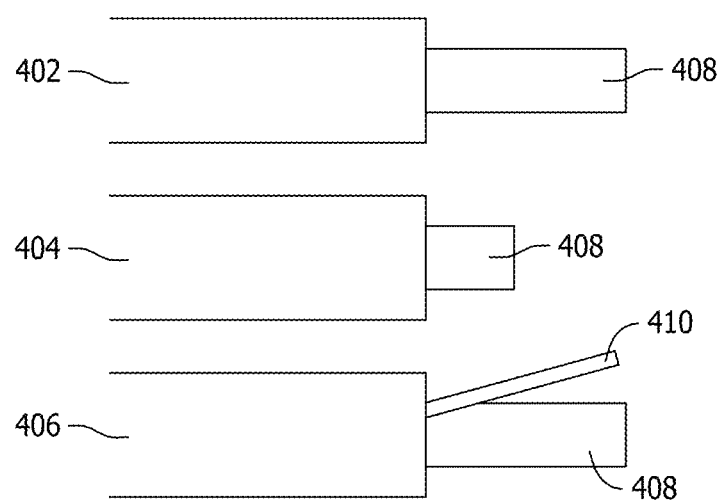
FIG. 2 is a schematic diagram of a plurality of stripped wire segments.

Strip and crimp inspection stations 324 and 326 facilitate ensuring that strip and crimp operations are performed properly using system 300. For example, FIG. 2 is a schematic diagram of a first stripped wire segment 402, a second stripped wire second segment 404, and a third stripped wire segment 406. Each stripped wire segment 402, 404, and 406 includes an exposed conductor 408. As shown in FIG. 2, however, only first stripped wire segment 402 shows a properly stripped wire. In second stripped wire segment 404, exposed conductor 408 is too short, and in third stripped wire segment 406, exposed conductor 408 includes a stray portion 410.

Figure 3:
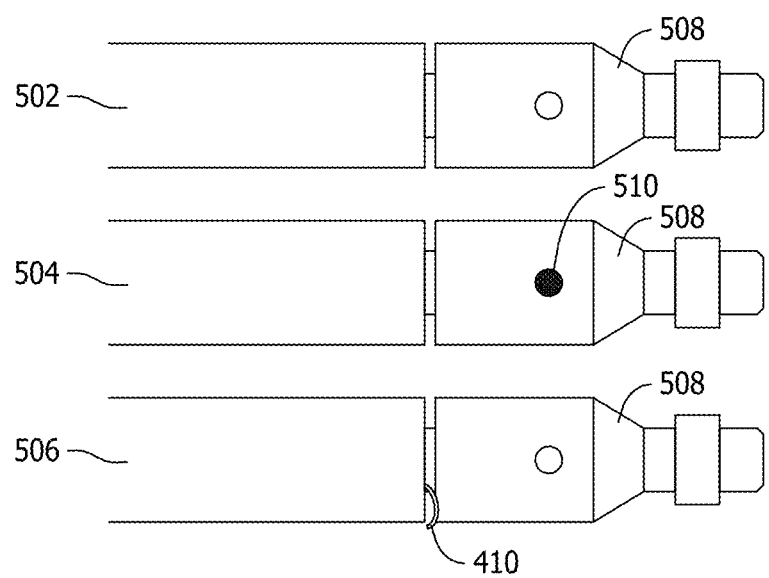
FIG. 3 is a schematic diagram of a plurality of crimped wire segments.

FIG. 3 is a schematic diagram of a first crimped wire segment 502, a second crimped wire segment 504, and a third crimped wire segment 506. Each crimped wire segment 502, 504, and 506 includes a connector 508 attached to exposed conductor 408. As shown in FIG. 3, however, only first crimped wire segment 502 shows a properly crimped wire. In second crimped wire segment 504, exposed conductor 408 is too short (as is evidenced by exposed conductor 408 not being visible through an inspection hole 510 in connector 508) and prevents connector 508 from being properly attached, and in third crimped wire segment 506, stray portion 410 of exposed conductor 408 interferes with the attachment of connector 508.

Accordingly, it is desirable to identify defects such as those shown in second stripped wire segment 404, third stripped wire segment 406, second crimped wire segment 504, and third crimped wire segment 506. However, at least some defects are only detectable when viewing a particular side of a wire segment 304. As such, a complete inspection system should either rotate wire segment 304 to view all sides, or must use an optical system that enables viewing multiple sides simultaneously without rotating wire segment 304. Further, system 300 handles different types of wire segments 304 and contacts. For example, wire segments 304 may vary in length, gauge, insulation type, contact type, and intended use. Accordingly, a single visual template of one corrected strip or crimp operation is not sufficient. Rather, an inspection machine (or technician) must be able to tell what type of wire segment 304 is being inspected and what quality standards should be used during inspection.

The implementations described herein provide an improved wire segment inspection system, as described herein. The inspection system described herein facilitates viewing an odd number of sides of a wire segment, and can be built with a relatively simple pyramid structure (e.g., a pentagonal pyramidal frustum) that can be fabricated, for example, using a three-dimensional printer. Further, the inspection system uses simple mirrors attached to the interior of an odd-sided pyramid, and does not require prisms. Self-reflections and interfering reflections are also eliminated using the inspection system described herein. Moreover, to view multiple sides of a wire segment, a single high-resolution camera or multiple lower resolution digital microscopes may be used. Further, the type of wire segment may be determined without reading a barcode on the wire segment. In the inspection system, light sources may be directly attached to a camera without generating directly reflected rays in the camera's view. Moreover, air flow or positive pressure may be used to facilitate minimizing dust and debris from entering an area of one or more mirrors, and to facilitate cooling cameras or microscopes in the system.

The systems and methods described herein provide improvements for an optical design and an interface design of an automated wire inspection system. In some implementations, a single camera is used to create a composite image of reflections of the wire. In other implementations, a multi-camera approach is used, in which each mirror has a corresponding digital camera imaging its reflection.

Optics for use in single camera implementations will now be described. Optics for multi-camera implementations will then be described. Aspects of the optical design for single camera implementations include a pyramid of mirrors, angles of the mirrors, a focal plane array for the camera, and a circular light source, as described herein.

For automated inspection, it is desirable to image all sides of a relatively short length of wire and insulation. In the exemplary implementation, the wire segment length to be viewed has a total length of approximately 3 centimeters (cm), including an insulated portion having a length of approximately 2 cm and a bare wire portion (that may include a connector) of approximately 1 cm. Alternatively, the implementations described herein may be scaled to accommodate wire segments having any suitable length. For inspection, the wire segment is inserted into the automated wire inspection system, imaged, and processed to produce quality measurements which can be used to accept or reject the stripping and/or crimping of the segment.

Figure 4:
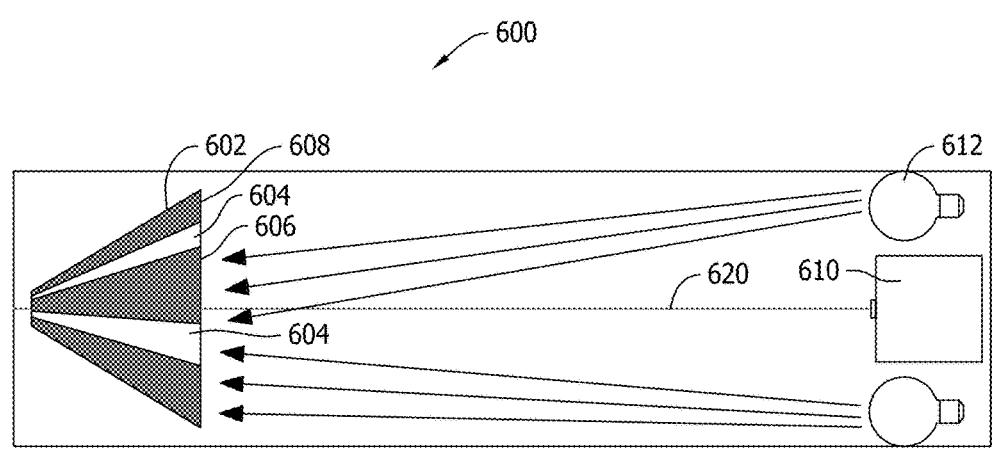
FIG. 4 is a schematic diagram of an exemplary wire inspection system.

FIG. 4 is a schematic diagram of an exemplary wire inspection system 600. To inspect the wire segment, the wire segment is surrounded by a mirror assembly 602 that includes an inverted pyramid of mirrors 604, as described herein. To avoid one mirror 604 viewing both the wire and another mirror 604, mirror assembly 602 includes an odd number of sides 606. The odd number of sides also facilitates avoiding self-reflections. In the exemplary implementation, each side 606 of mirror assembly 602 includes a trapezoidal mirror 604 in a center portion of side 606 and non-reflecting surfaces 608 (e.g., diffusely reflecting paint) on outer portions of side 606. This facilitates ensuring that each mirror 604 viewing the wire segment sees a relatively uniform non-specular reflecting background. As shown in FIG. 4, system 600 includes a single camera 610 and a light source 612. Light source 612 is substantially circular, and surrounds camera 610.

Figure 5:
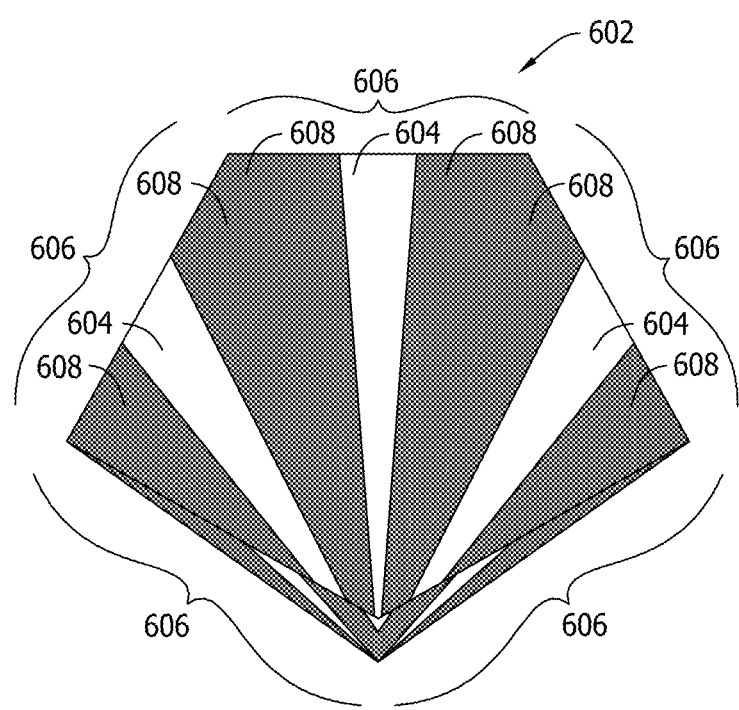
FIG. 5 is a perspective view of an exemplary mirror assembly that may be used with the wire inspection system shown in FIG. 4.
Figure 6:
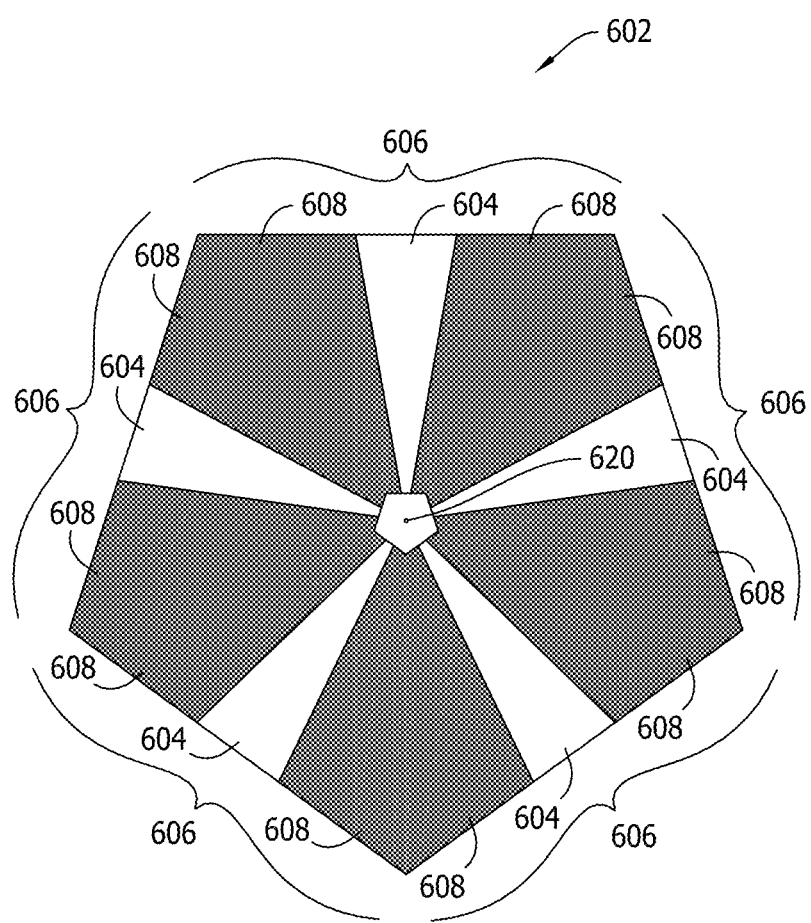
FIG. 6 is an end view of the mirror assembly shown in FIG. 5.

FIG. 5 is a perspective view of mirror assembly 602, and FIG. 6 is an end view of mirror assembly 602. Mirror assembly 602 is aligned with a center axis 620 of system 600. As seen best in FIG. 6, relative to center axis 620, each mirror 604 is opposite a non-reflecting surface 608. This prevents self-reflections occurring from having mirrors 604 directly opposite one another.

Figure 7:
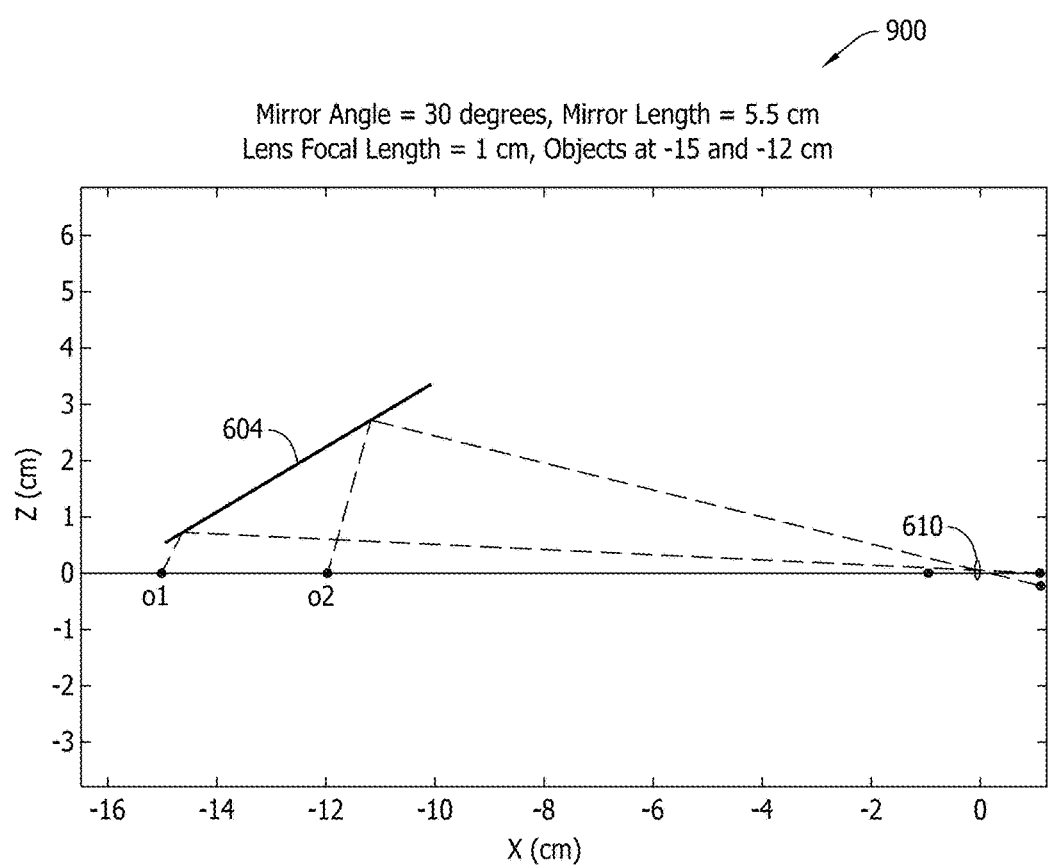
FIG. 7 is a graph showing an exemplary viewing geometry.

FIG. 7 is a graph 900 showing a viewing geometry for one mirror 604 with single camera 610 in system 600. Specifically, graph 900 shows the optical geometry when viewing a wire end two object points, o1 and o2, on an optical axis, where a single mirror 604 reflects light from the wire into camera 610 at x=0 and produces an image to the right of a lens of camera 610. The dots on the optical axis on either side of camera 610 indicate the focal points of the lens. Other mirrors 604 in mirror assembly 602 produce similar symmetric images about the optical axis.

As shown in graph 900, an optical path from an object to the lens includes a first portion from the object to mirror 604 and a second portion from mirror 604 to the lens. Accordingly, the object can be modeled as being at a distance from the lens which is the sum of the object to mirror distance and the mirror to lens distance along the ray path. This then defines half of a field of view (FOV) of camera 610—the other half FOV accounts for rays reflected from other mirrors 604 in mirror assembly 602. The path length difference between the two rays (i.e., the ray from o1 to the lens, and the ray from o2 to the lens) may be, for example, less than 2 cm, which defines a required depth of field. The path length difference depends on the angle of mirror 604 relative to center axis 620. For angles near 45°, the path length difference is near zero.

From analysis of single camera implementations, it follows that object distance to lens and lens focal length (FL) are interdependent. Specifically, these two parameters determine a required angular FOV, image size on a focal plane array (FPA), and distance from lens to FPA. It follows that (f-number of lens)=(focal length)/(aperture diameter). This has a relatively large effect on the depth of field, a geometrical optics ray bundle standard deviation, and a diffraction limited blur spot size. A relatively small f-number (i.e., a large aperture relative to focal length) implies a relatively small diffraction limited blur spot, but reduced depth of field and increased geometrical optics ray bundle standard deviation.

Focus distance of the image on the FPA depends on both the distance to the object and the angle that a ray from the object makes with the lens. Relatively short focal length lenses require short distances to objects to have an image fill the FPA and wide angular FOV. A wide FOV typically requires improved lens design as compared to a narrow FOV, to maintain good focus across the entire FOV. However, after a certain point, lengthening the FL does not improve performance, because the diffraction limited blur spot size increases directly with FL and dominates the geometrical ray bundle size for a well-designed system. An efficient lens design minimizes this angle dependent change in focal distance.

Figure 8:
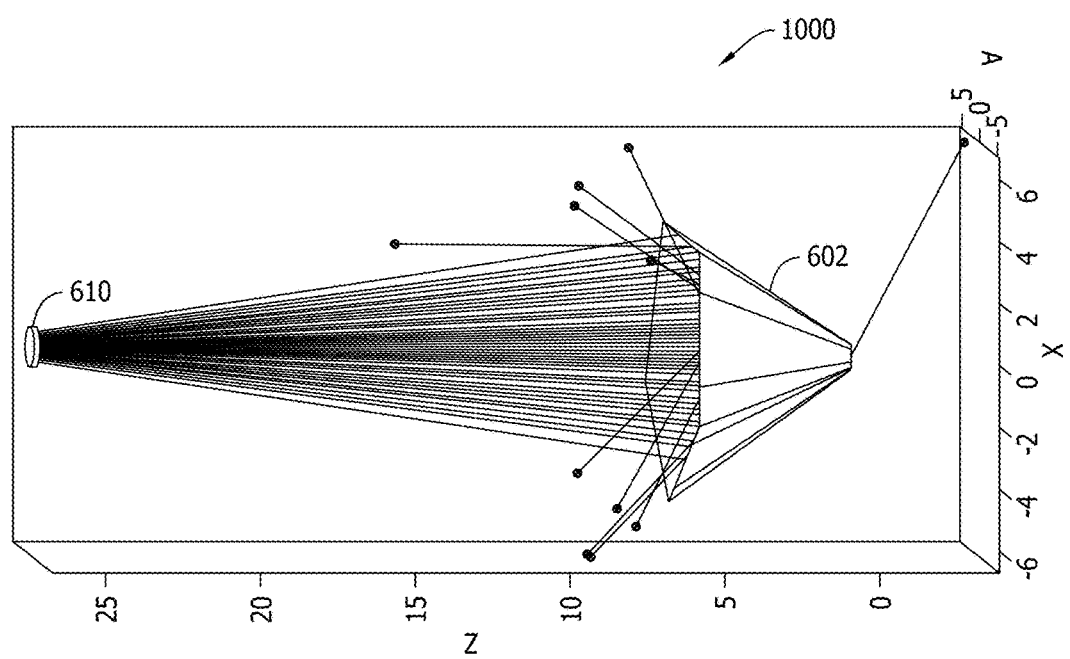
FIG. 8 is a graph showing ray tracing simulation results.

A ray tracing analysis was used to examine mirror assembly 602 to check for self-reflection and direct light source reflections to determine whether camera 610 self-images itself in the mirror. FIG. 8 is a graph 1000 representing such a simulation.

In the exemplary implementation, the angle of each mirror 604 is defined as the angle that mirror 604 and corresponding side 606 make with center axis 620 of mirror assembly 602. The angle affects the required depth of field because the path length difference between both ends of an object (e.g., the wire segment) changes with the mirror angle. The path length difference is substantially zero when the mirror angle is 45°, but the focal point of a lens may be different because of different ray incidence angles on the lens for different ray incidence angles along the wire segment length. For mirror angles less than 20°, the path length difference is generally less than 2 cm for a 3 cm long wire segment.

The required length of mirror 604 implies that, as the mirror angle becomes less, the mirror length must become longer to reflect a ray from a tip of the wire segment to the lens. The FOV of camera 610 implies that as the mirror angle becomes larger, a diameter of mirror assembly 602 and the FOV of camera 610 become larger. This has a relatively small effect on the image size on the FPA. The focal distances for both ends of the wire segment depend on the mirror angle. For the end further from camera 610, the focal distance is nearly constant across different angles because of relatively small incidence angles and relatively small changes in path length. In contrast, for the end near camera 610, the focal distance changes significantly due to larger incidence angles and larger changes in path length. In one example, a mirror angle of approximately 27° corresponds to equal focal distances for both ends. However, depending on the focal length of the lens, the f-number of the lens, and the lens configuration, this mirror angle may differ.

Figure 9:
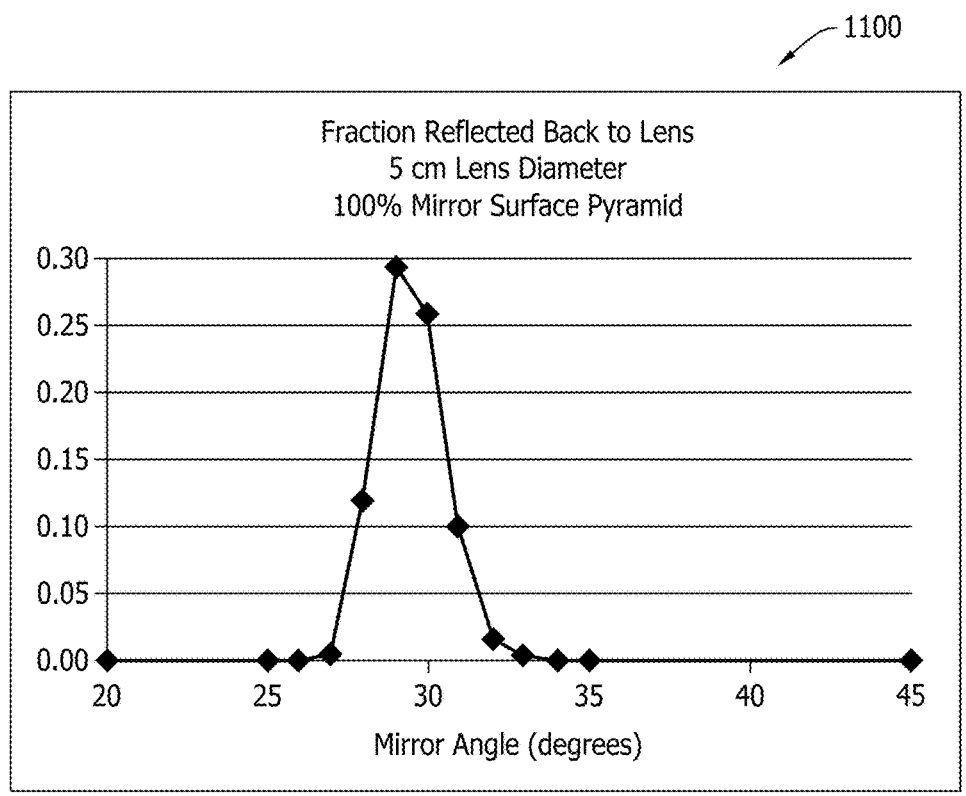
FIG. 9 is a graph showing ray tracing simulation results.

FIG. 9 is a graph 1100 showing a ray tracing simulation that shows a fractions of rays reflected back to camera 610 as a function of mirror angle. As shown in graph 1100, except for mirror angles ranging from approximately 26° to approximately 34°, because no light is reflected back to the lens, the pyramid of mirror assembly 602 may be totally covered with mirrors. Further, as shown in graph 1100, the peak reflection occurs near a 29° mirror angle (referred to as a peak mirror angle), with nearly 30% of rays reflected back. It is expected that the peak mirror angle and peak reflection will be different for mirror assemblies having a different number of sides.

Figure 10:
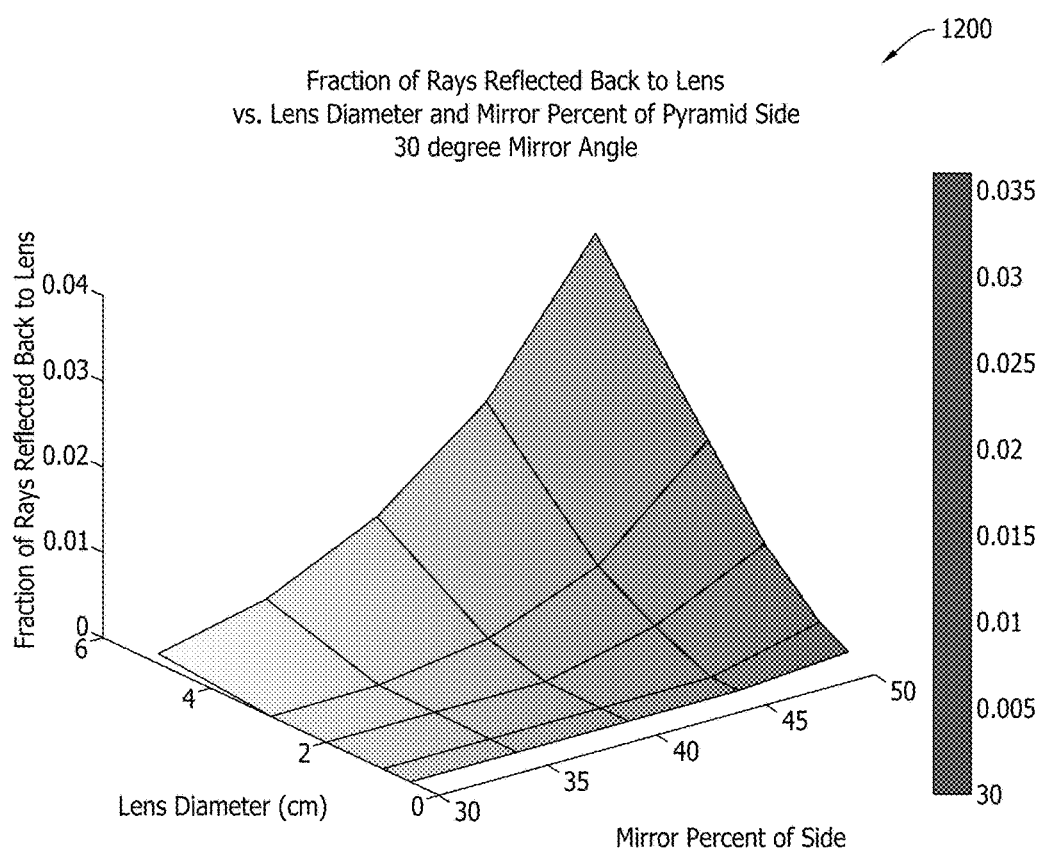
FIG. 10 is a graph showing ray reflections.

FIG. 10 is a graph 1200 demonstrating rays reflected when the relative mirror size and lens diameter are varied while maintaining a 30° mirror angle. As demonstrated by graphs 1100 and 1200, there is essentially no camera self-imaging for mirror angles less than approximately 26° and greater than approximately 34° (up to 45°), independent of the fraction of a side 406 that includes a mirror 604. Within the range of approximately 26° to approximately 34°, certain angles may be used with caution for selected lens diameters and fractions of sides 606 that are mirrors 604 while still avoiding self-imaging, assuming that the mirror fraction is limited to less than 50% to avoid multiple images of the wire segment.

A limiting factor on image resolution is the FPA size. Specifically, an FPA with more pixels having the same pitch allows the image of the wire segment to be physically larger with the same field of view, while the blur spot depends on the lens diameter, not the FPA size. For example, performance of a 2048×2048 5.5 micrometer pixel pitch FPA is slightly better than for a 1280×1024 5.3 micrometer pixel pitch FPA. For bigger FPAs, the wire segment must be moved closer to the lens to fill the FPA. This creates larger angles for the ray from the wire segment to camera 610, which causes larger ray bundle diameters for a given f-number, mostly negating the effects of the larger image when using poorer lenses. However, with a relatively sophisticated lens on camera 610, the result is that larger FPAs yield better results.

In the exemplary implementation, light source 612 is a circular illumination source, such as a round light tube. Alternatively, light source 612 may be any type of lighting device that enables inspection system 600 to function as described herein. In the exemplary implementation, a diameter of light source 612 ranges from the diameter of the lens of camera 610 to 2 cm larger than the lens diameter. For example, light source 612 may have a diameter ranging from approximately 9 cm to 10 cm. For simulation purposes, a square lens was used. Accordingly, the lower range of the diameter of light source 612 was set as the length of a side of the square lens divided by the square root of two, plus a small margin to place light source 612 outside corners of the square lens. During the simulation, no reflections were found for the light source into the lens for 20°, 25°, 35°, 40°, and 45° degree mirror angles with mirror 604 covering approximately 30% to 50% of each side 606. However, some reflections occurred for mirror angles between 26° and 34°. Thus, light source 612 is feasible for a relatively large variety of potential design sizes.

Figure 11:
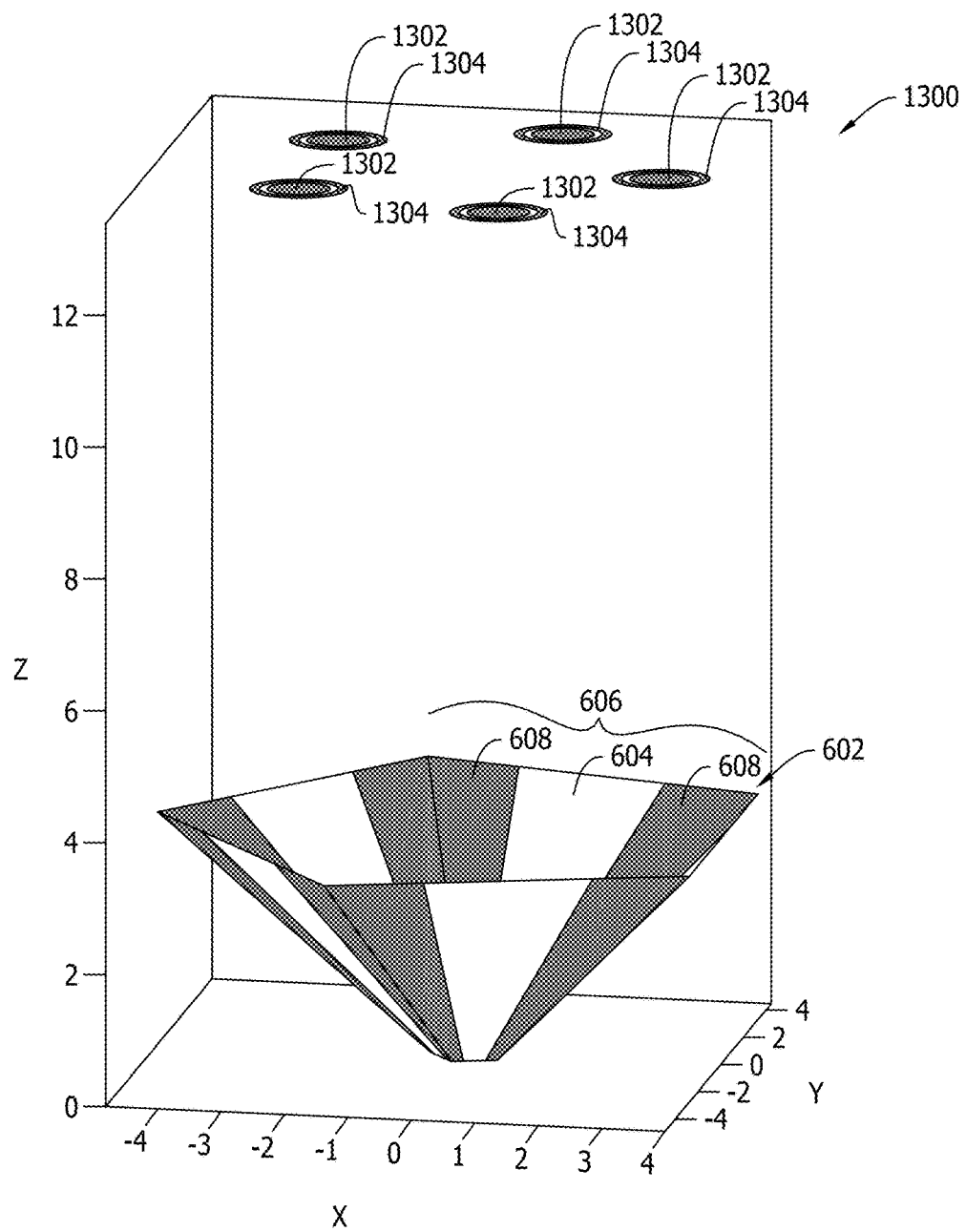
FIG. 11 is a schematic diagram of an alternative exemplary wire inspection system.

FIG. 11 is a schematic diagram of an alternative implementation of a wire inspection system 1300 that uses multiple digital microscopes 1302. In the exemplary implementation, system 1300 includes a digital microscope 1302 for each mirror 604 on mirror assembly 602. Accordingly, each digital microscope 1302 essentially views a single mirror 604 (although there will be some spillover of the field of view of digital microscope 1302 to other mirrors). This configuration requires that digital microscopes 1302 not see their own reflection or multiple reflections of the wire segment. Each microscope 1302 includes a ring 1304 of light emitting diodes (LEDs) in the exemplary implementation. The reflections from rings 1304 are a function of a distance of digital microscope 1302 from mirror assembly 602 and the fraction of an associated side 606 occupied by mirror 604. Further, a FOV and lens diameter of digital microscope 1302 are also to be considered.

Ray tracing studies have demonstrated that for a digital microscope, such as digital microscopes 1302, a minimum distance between the digital microscope and the object being imaged that is greater than approximately 10 cm avoids multiple images of the wire segment and self-image or imaging light sources. The mirror angle of mirrors 604 is approximately 45° such that mirror assembly 402 can fit within a relatively narrow region (e.g., approximately 10 cm), which makes packaging system 1300 within system 300 (shown in FIG. 3) relatively easy.

Figure 12:
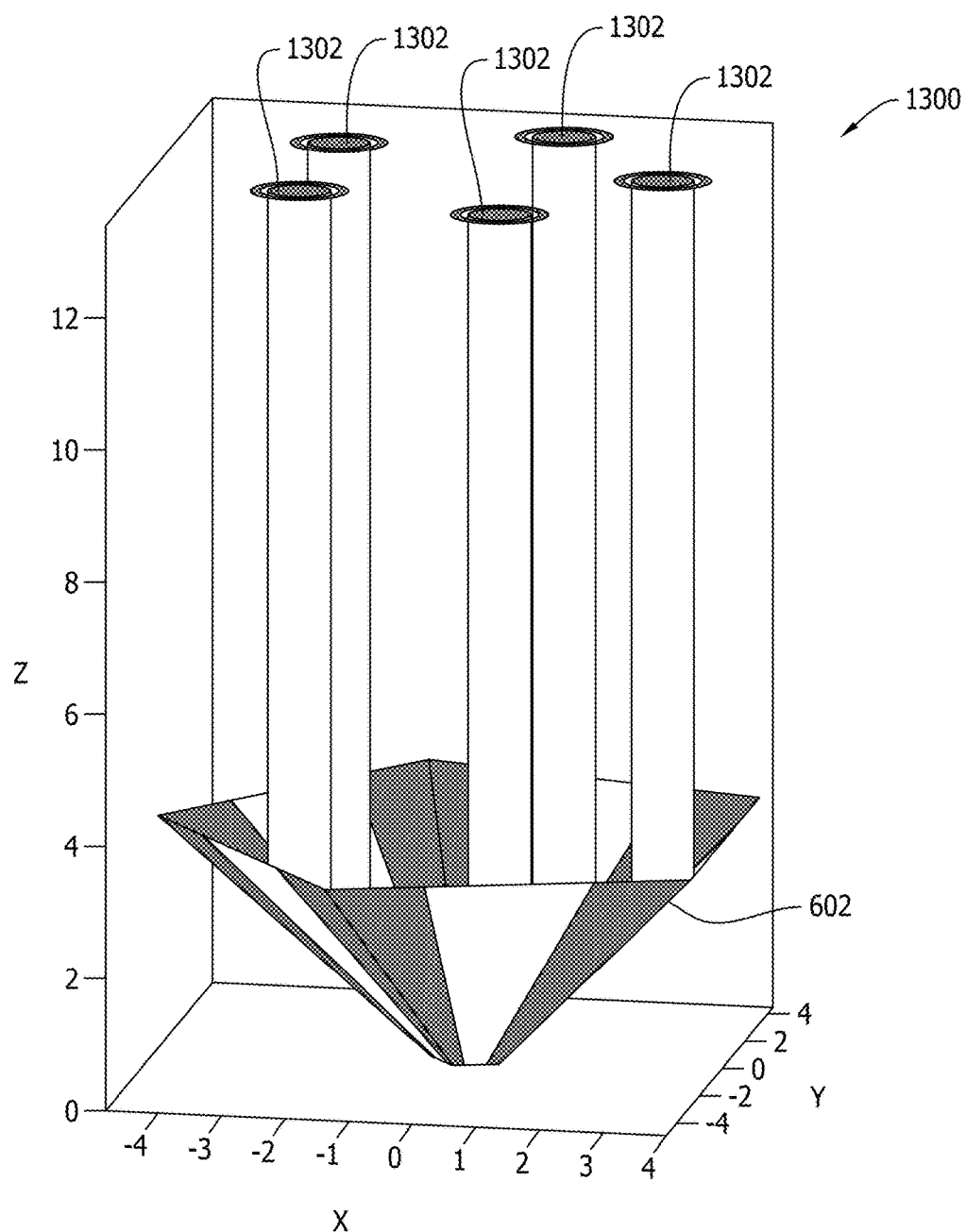
FIG. 12 is a diagram illustrating ray reflections in the wire inspection system shown in FIG. 11.
Figure 13:
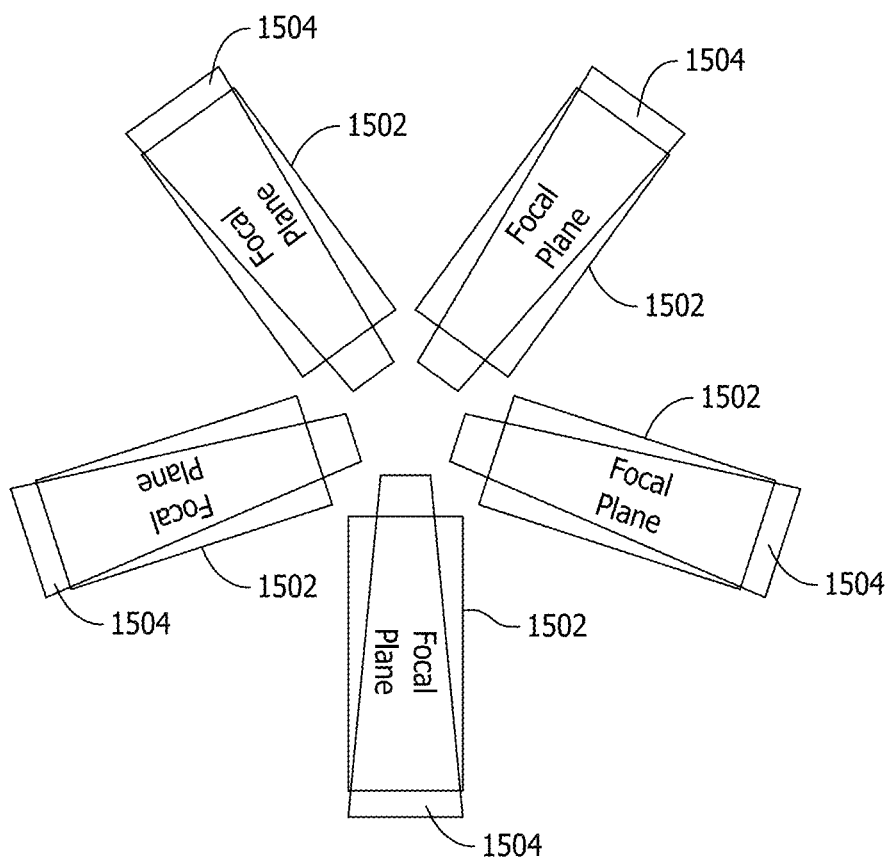
FIG. 13 is a diagram showing an exemplary orientation of focal planes and arrays in the wire inspection system shown in FIG. 11.

FIG. 12 is a diagram illustrating how rays from the wire segment are reflected by mirrors 604 and incident on digital microscopes 1302. As shown in FIG. 12, different sides of the wire are imaged by different digital microscopes 1302. To align the images seen by each digital microscope 1302, rectangular sensor arrays for each microscope may be oriented such that each array is oriented at approximately 72° with respect to adjacent arrays. FIG. 13 is a diagram showing such an orientation of arrays 1502 and focal planes 1504 incident upon each array 1502. This configuration facilitates reducing requirements on camera pixel size and number for a given resolution relative to imaging using single camera 610 (shown in FIG. 6).

With the configuration described herein, substantially independent of the fraction of sides 606 covered by mirrors 604, digital microscopes 1302 will not see themselves (or associated rings 1304), or produce multiple images of the wire segment if the distance from digital microscopes 1302 to mirror assembly 602 is greater than 10 cm. These results are generally not achievable using a single camera configuration (shown in FIG. 4).

Figure 14:
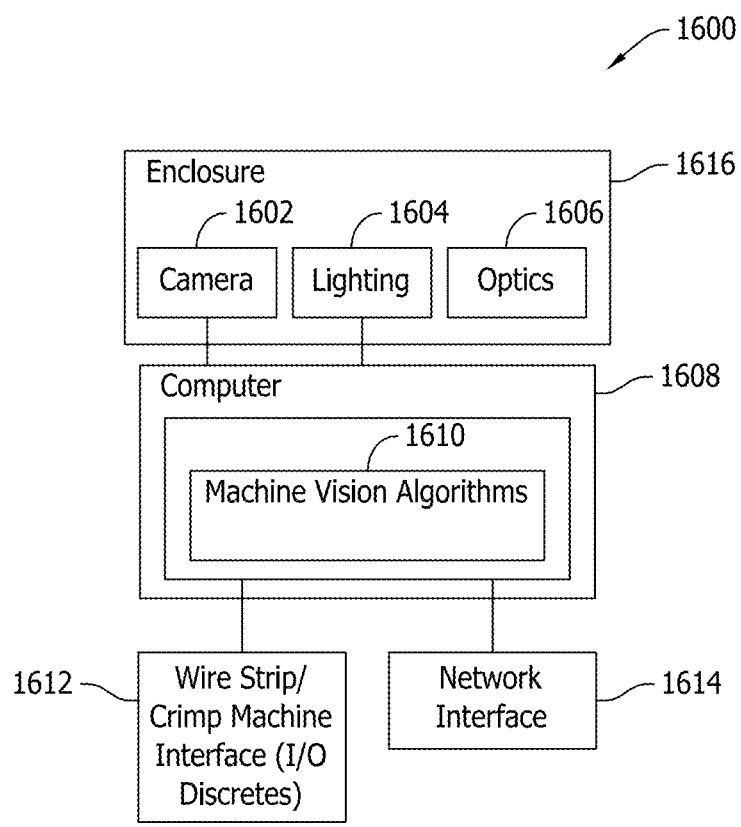
FIG. 14 is a block diagram of an exemplary inspection station.

FIG. 14 is a block diagram of an exemplary inspection station 1600, such as strip and crimp inspection stations 324 and 326 (shown in FIG. 1). Each station includes a camera system 1602, a lighting system 1604, an optics system 1606, a computer 1608 having machine vision algorithms 1610 stored thereon, a wire strip/crimp machine interface 1612, a network interface 1614, and a physical package or enclosure 1616 that uses positive air pressure to keep dust out.

In the exemplary implementation, camera system 1602 includes a single high resolution camera having a network interface, such as camera 610 (shown in FIG. 4), or a system of digital microscope cameras each having a network interface, such as digital microscopes 1302 (shown in FIG. 11).

Lighting system 1604 illuminates the wire segment being inspected, such that the wire segment diffusely reflects light onto the mirrors and then towards the camera(s). Lighting system 1604 avoids large mirror self-reflections that might otherwise pollute the detected wire image.

Optics system 1606 includes an odd-sided pyramid in the exemplary implementation, as described above. For each side, mirrors cover less than half of each side, and the remainder of each side has a non-reflective surface. The mirrors are used to transmit images of all sides of each wire segment towards the camera(s).

Computer 1608 includes machine vision algorithms 1610 for automatically inspecting the images acquired by the camera(s) and outputting quality information for the wire segments based on the inspection.

In the exemplary implementation, wire strip/crimp machine interface 1612 includes a set of discrete input/output (I/O) connections that are programmed to communicate with wire inspection system 300 (shown in FIG. 1) to control when the inspection occurs (e.g., when the wire segment is inserted into the inspection hole). The set of discrete input/output (I/O) connections also communicate what types of wire segments and crimps are present so as to better assess the quality of the strip and/or crimp.

Network interface 1614 is a digital interface between computer 1608 and a database (not shown) that includes wire information and associated quality reports in the exemplary implementation.

Enclosure 1616, in the exemplary implementation, is a container that includes fans and filters for providing positive air pressure that enables clean air flow around the camera(s) for cooling purposes, and across mirror surfaces to keep the surfaces relatively dust-free. As shown in FIG. 14, in the exemplary implementation, enclosure 1616 packages camera system 1602, lighting system 1604, and optics system 1606 separate from computer 1608. Alternatively, enclosure 1616 may package computer 1608 with camera system 1602, lighting system 1604, and optics system 1606.

Figure 15:
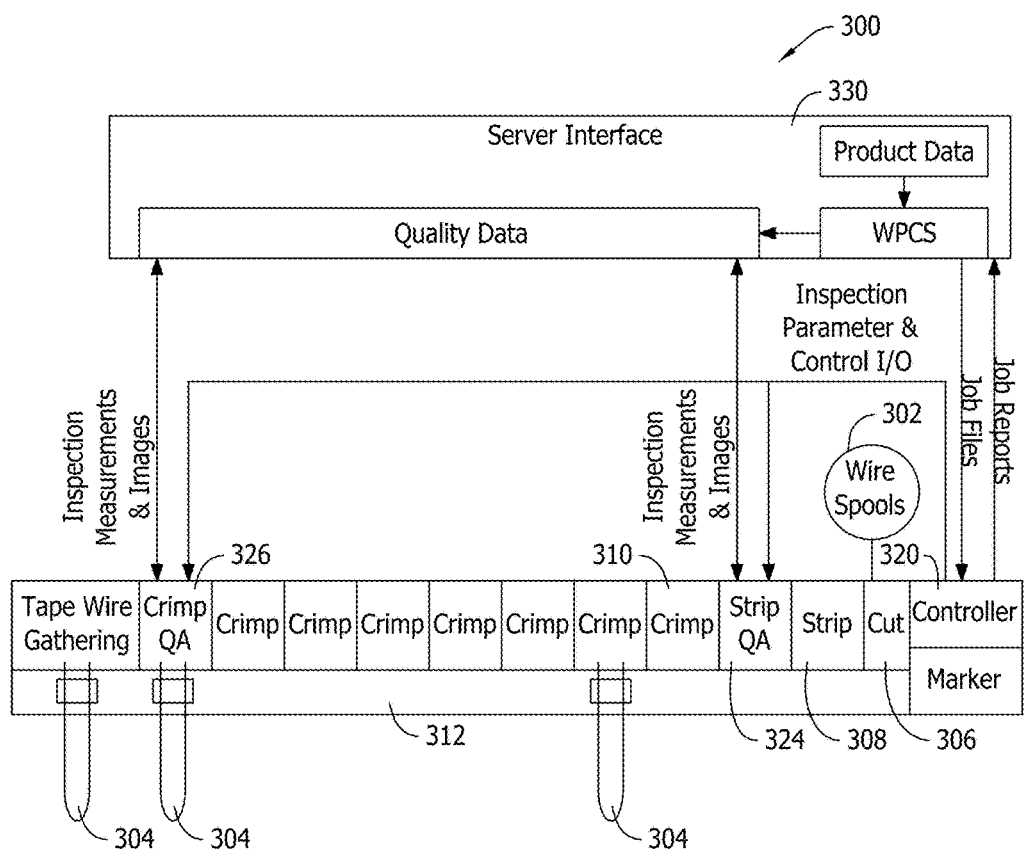
FIG. 15 is a diagram illustrating exemplary data communications in the wire segment processing system shown in FIG. 1.

FIG. 15 is a diagram illustrating data communications in wire segment processing system 300. In the exemplary implementation, two different types of data are passed between strip station 308, crimp station 310, strip inspection station 324, and crimp inspection station 326: wire information (which may include connector information) and control information.

In at least some known wire segment processing systems, inspection stations read a wire label (e.g., a barcode) on the wire segment to gather wire information. Typically, the wire label is applied every 4 inches (10.6 centimeters) along one side of the wire. Accordingly, to ensure that the wire segments include the wire label, the wire segments may be relatively long in known systems.

In the exemplary implementation, to avoid performing optical character recognition along a curved surface of a wire segment in an unknown orientation, controller 320 communicates wire information to strip inspection station 324 and/or crimp inspection station 326. For example, controller 320 may use discrete I/O signals to signal the wire information, and strip inspection station 324 and/or crimp inspection station 326 may use a lookup table to determine the wire information from the discrete I/O signals. In another example, controller 320 transmits the wire information over a separate communication line between controller 320 and strip inspection station 324 and/or crimp inspection station 326.

Figure 16:
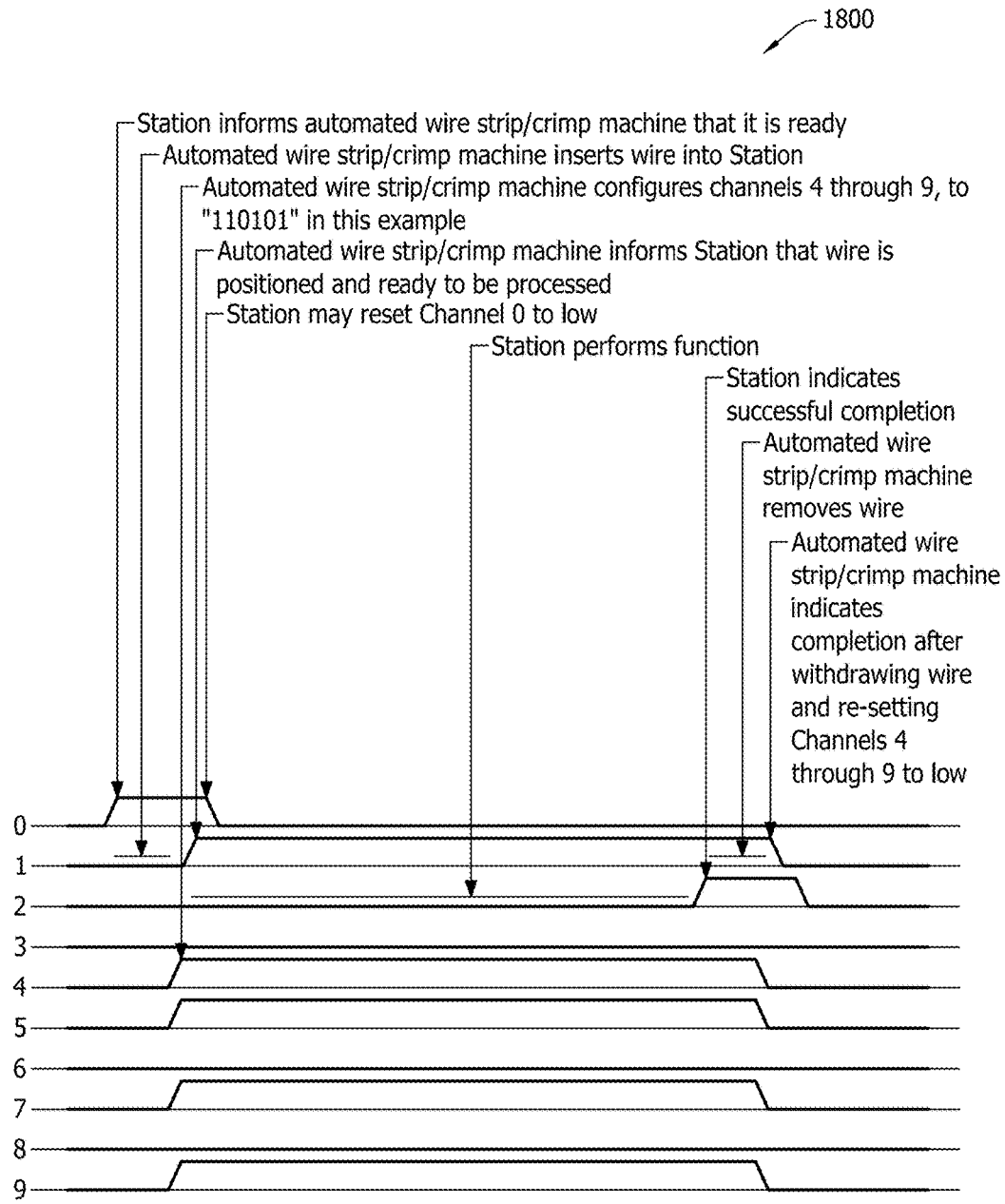
FIG. 16 is a diagram of an exemplary control signal interface.

Control information can be exchanged similarly within wire segment processing system 300 (e.g., using discrete I/O signals and/or a separate communication line). FIG. 16 shows an exemplary control signal interface 1800 that may be implemented in system 300 to exchange control information. Control signal interface 1800 also allows operation of strip inspection station 324 and/or crimp inspection station 326 to be stopped if internal error conditions occur. In alternative implementations, any alternative communications network that communicates with strip station 308 and/or crimp station 310 may be used with a digital protocol that implements commands similar to those shown in FIG. 16.

In the implementations described herein, images taken of wire segments may be saved on a computing device communicatively coupled to strip inspection station 324 and/or crimp inspection station 326 across a network. Decision metrics may also be stored on the computing device, such that performance data may be gathered regarding operation of strip inspection station 324 and/or crimp inspection station 326 in order to improve performance of wire segment processing system 300.

Further, in some implementations, polarizing filters may be used with the light sources and/or cameras described herein to facilitate minimizing direct reflections off of relatively shiny surfaces. For example, in some implementations, a light source and/or camera may include a pair of polarizing filters arranged normal with respect to each other such that spectral highlights reflected from relatively shiny wire and/or contact surfaces on a wire segment are cross polarized and canceled out before an image is acquired by the camera. In some implementations, when a single camera is used, to facilitate reducing direct reflections and ensuring cross polarization, polarized light sources may be oriented to shine directly onto the wire segment, instead of reflecting off of the mirrors. Further, in implementations using one light source and one mirror for each of multiple cameras, polarizers may be used to cross polarize spectral highlights for each camera/light source/mirror optical path.

Figure 17:
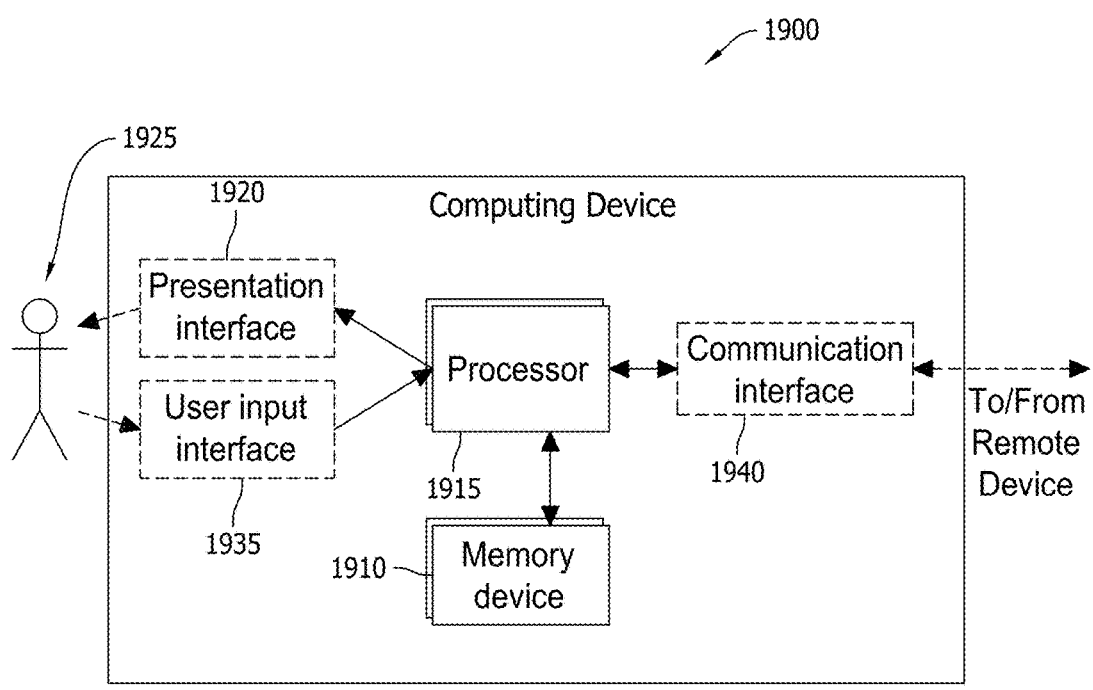
FIG. 17 is a block diagram of an example computing device that may be used with the wire segment processing system shown in FIG. 1.

FIG. 17 is a block diagram of a computing device 1900 that may be used with the implementations described herein. For example, controller 320, server 322, and/or computer 1608 may be implemented using computing device 1900. Computing device 1900 includes at least one memory device 1910 and a processor 1915 that is coupled to memory device 1910 for executing instructions. In some implementations, executable instructions are stored in memory device 1910. In the example implementation, computing device 1900 performs one or more operations described herein by programming processor 1915. For example, processor 1915 may be programmed by encoding an operation as one or more executable instructions and by providing the executable instructions in memory device 1910.

Processor 1915 may include one or more processing units (e.g., in a multi-core configuration). Further, processor 1915 may be implemented using one or more heterogeneous processor systems in which a main processor is present with secondary processors on a single chip. In another illustrative example, processor 1915 may be a symmetric multi-processor system containing multiple processors of the same type. Further, processor 1915 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

In the example implementation, memory device 1910 is one or more devices that enable information such as executable instructions and/or other data to be stored and retrieved. Memory device 1910 may include one or more computer readable media, such as, without limitation, dynamic random access memory (DRAM), static random access memory (SRAM), a solid state disk, and/or a hard disk. Memory device 1910 may be configured to store, without limitation, application source code, application object code, source code portions of interest, object code portions of interest, configuration data, execution events and/or any other type of data.

In the example implementation, computing device 1900 includes a presentation interface 1920 that is coupled to processor 1915. Presentation interface 1920 presents information to a user 1925. For example, presentation interface 1920 may include a display adapter (not shown) that may be coupled to a display device, such as a cathode ray tube (CRT), a liquid crystal display (LCD), an organic LED (OLED) display, and/or an "electronic ink" display. In some implementations, presentation interface 1920 includes one or more display devices.

In the example implementation, computing device 1900 includes a user input interface 1935. User input interface 1935 is coupled to processor 1915 and receives input from user 1925. User input interface 1935 may include, for example, a keyboard, a pointing device, a mouse, a stylus, a touch sensitive panel (e.g., a touch pad or a touch screen), a gyroscope, an accelerometer, a position detector, and/or an audio user input interface. A single component, such as a touch screen, may function as both a display device of presentation interface 1920 and user input interface 1935.

Computing device 1900, in the example implementation, includes a communication interface 1940 coupled to processor 1915. Communication interface 1940 communicates with one or more remote devices. To communicate with remote devices, communication interface 1940 may include, for example, a wired network adapter, a wireless network adapter, and/or a mobile telecommunications adapter.

Figure 18:
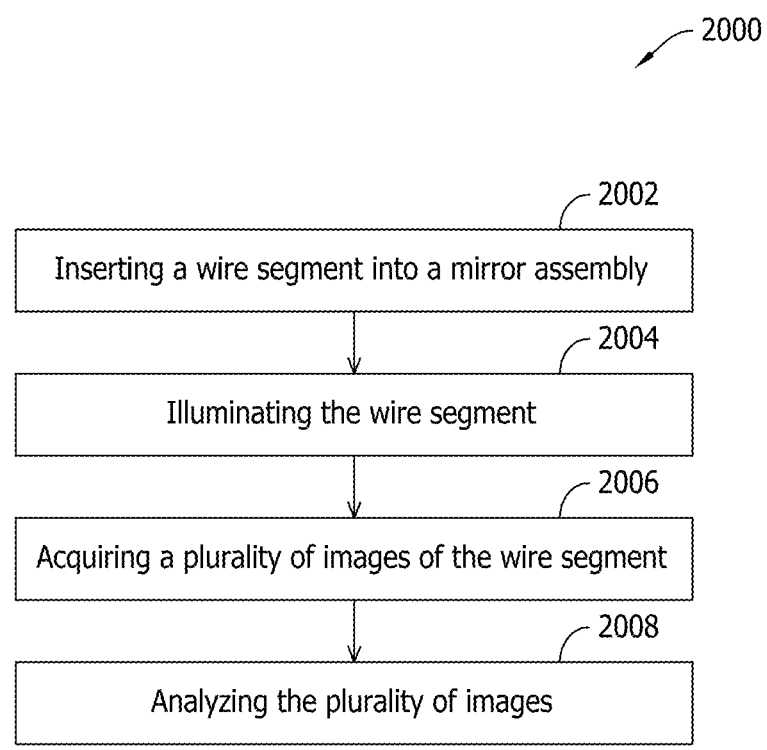
FIG. 18 is a flowchart of an exemplary method for inspecting a wire using the wire inspection system shown in FIG. 4.

FIG. 18 is a flowchart of an exemplary method 2000 for inspecting a wire segment. Method 2000 may be implemented, for example, using wire segment processing system 300 (shown in FIG. 1), inspection station 1600 (shown in FIG. 14), and/or computing device 1900 (shown in FIG. 17). Method 2000 includes inserting 2002 the wire segment into a mirror assembly, such as mirror assembly 602 (shown in FIG. 4). The wire segment is illuminated 2004 using a light source, and a plurality of images are acquired 2006. For example, the plurality of images may be acquired 2006 using single camera 610 (shown in FIG. 4) or digital microscopes 1302 (shown in FIG. 11).

The acquired images are analyzed 2008 using a computing device, such as computer 1608 using machine vision algorithms 1610 (both shown in FIG. 14). Specifically, in the exemplary implementation, the images are analyzed to assess at least one of a strip quality and a crimp quality of the wire segment. To analyze the acquired images, any suitable image analysis technique may be implemented. In the exemplary implementation, each image is analyzed separately.

For example, in one implementation, the computing device may identify portions of the image that have a copper color, and categorize those portions as corresponding to an exposed conductor. By determining the portions of the image that include a copper coloration, the dimensions (e.g., length, width) of the exposed conductor can be calculated to determine whether the exposed conductor has the appropriate length, width, etc. (See, e.g., first and second stripped wire segments 402 and 404 (shown in FIG. 2)).

In another implementation, the computing device may analyze the image to determine whether portions of the wire segment fall outside of a predetermined boundary, or perimeter. This may facilitate identifying stray portions, such as stray portion 410 (shown in FIG. 2). In yet another implementation, the computing device compares the acquired image to a reference image to assess the strip and/or crimp quality. In some embodiments, based on the analysis, the computing device outputs a notification indicating whether or not the strip and/or crimp quality is satisfactory.

Figure 19:
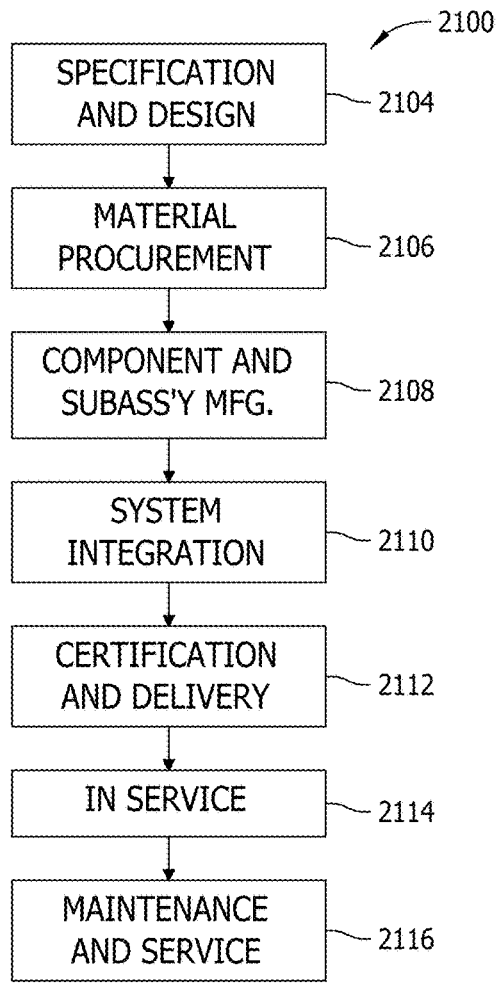
FIG. 19 is a flow diagram of an exemplary aircraft production and service method.
Figure 20:
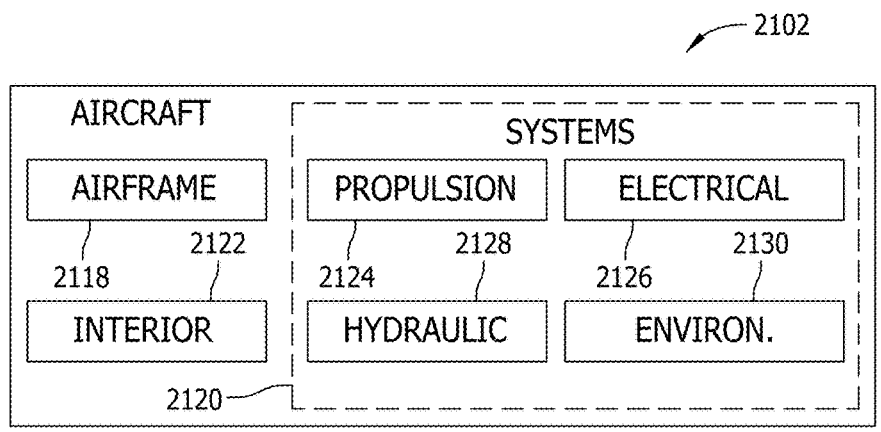
FIG. 20 is a block diagram of an exemplary aircraft.

Implementations of the disclosure may be described in the context of an aircraft manufacturing and service method 2100 (shown in FIG. 19) and via an aircraft 2102 (shown in FIG. 20). During pre-production, including specification and design 2104 data of aircraft 2102 may be used during the manufacturing process and other materials associated with the airframe may be procured 2106. During production, component and subassembly manufacturing 2108 and system integration 2110 of aircraft 2102 occurs, prior to aircraft 2102 entering its certification and delivery process 2112. Upon successful satisfaction and completion of airframe certification, aircraft 2102 may be placed in service 2114. While in service by a customer, aircraft 2102 is scheduled for periodic, routine, and scheduled maintenance and service 2116, including any modification, reconfiguration, and/or refurbishment, for example. In alternative implementations, manufacturing and service method 2100 may be implemented via platforms other than an aircraft.

Each portion and process associated with aircraft manufacturing and/or service 2100 may be performed or completed by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 20, aircraft 2102 produced via method 2100 may include an airframe 2118 having a plurality of systems 2120 and an interior 2122. Examples of high-level systems 2120 include one or more of a propulsion system 2124, an electrical system 2126, a hydraulic system 2128, and/or an environmental system 2130. Any number of other systems may be included.

The apparatus and methods embodied herein may be employed during any one or more of the stages of method 2100. For example, components or subassemblies corresponding to component and subassembly production process 2108 may be fabricated or manufactured in a manner similar to components or subassemblies produced while aircraft 2102 is in service 2114. Also, one or more apparatus implementations, method implementations, or a combination thereof may be utilized during the production stages 2108 and 2110, for example, by substantially expediting assembly of, and/or reducing the cost of assembly of aircraft 2102. Similarly, one or more of apparatus implementations, method implementations, or a combination thereof may be utilized while aircraft 2102 is being serviced or maintained, for example, during scheduled maintenance and service 2116.

As used herein, the term "aircraft" may include, but is not limited to only including, airplanes, unmanned aerial vehicles (UAVs), gliders, helicopters, and/or any other object that travels through airspace. Further, in an alternative implementation, the aircraft manufacturing and service method described herein may be used in any manufacturing and/or service operation.

The implementations described herein facilitate automated inspection of wire segments for strip and crimp quality. The implementations described herein are not limited to use with wire inspection systems, but may also be used for other applications that involve optical inspection of objects from multiple directions. Further, the systems and methods described herein facilitate inspecting wire segments of multiple wire types, and can be integrated with existing wire strip and crimp machines.

This written description uses examples to disclose various implementations, which include the best mode, to enable any person skilled in the art to practice those implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed:

1. A wire inspection system comprising:
   a mirror assembly comprising an odd number of sides greater than two arranged to form a pyramid structure configured to surround a wire segment, wherein a plurality of said sides comprise a mirror;
   wherein each mirror is sized to occupy less than half of a surface of an associated side;
   a light source configured to illuminate the wire segment; and
   at least one camera configured to acquire a plurality of images of the wire segment that are reflected by said plurality of mirrors, wherein each image of the plurality of images shows a different side of the wire segment.

2. A wire inspection system in accordance with claim 1, further comprising a computer communicatively coupled to said at least one camera and configured to assess a crimp quality of the wire segment based on the plurality of images.

3. A wire inspection system in accordance with claim 1, further comprising a computer communicatively coupled to said at least one camera and configured to assess a strip quality of the wire segment based on the plurality of images.

4. A wire inspection system in accordance with claim 1, wherein at least one of said light source and said at least one camera comprises a pair of polarizing filters.

5. A wire inspection system in accordance with claim 1, wherein each side of said mirror assembly comprises a mirror.

6. A wire inspection system in accordance with claim 1, further comprising a positive air pressure system configured to cool said at least one camera and configured to substantially prevent dust and dirt from entering an enclosure housing said plurality of mirrors.

7. A wire inspection system in accordance with claim 1, wherein said at least one camera comprises a single high-resolution camera.

8. A wire inspection system in accordance with claim 1, wherein said at least one camera comprises a plurality of digital microscopes.

9. An automated wire segment processing system comprising:
   at least one of a strip station configured to strip a wire segment and a crimp station configured to crimp the wire segment;
   a controller configured to control operation of said strip station and said crimp station; and
   a wire inspection system configured to assess at least one of a strip quality of a stripping operation performed on the wire segment by said strip station and a crimp quality of a crimping operation performed on the wire segment by said crimp station, said wire inspection system comprising:
   a mirror assembly comprising an odd number of sides greater than two arranged to form a pyramid structure configured to surround the wire segment, wherein a plurality of said sides comprise a mirror;
   wherein each mirror is sized to occupy less than half of a surface of an associated side;
   a light source configured to illuminate the wire segment; and
   at least one camera configured to acquire a plurality of images of the wire segment that are reflected by said plurality of mirrors, wherein each image of the plurality of images shows a different side of the wire segment.

10. An automated wire segment processing system in accordance with claim 9, wherein said controller is configured to transmit, to said wire inspection system, data indicative of characteristics of the wire segment.

11. An automated wire segment processing system in accordance with claim 9, wherein said mirror assembly comprises five sides.

12. An automated wire segment processing system in accordance with claim 9, wherein each side of said mirror assembly comprises a mirror.

13. An automated wire segment processing system in accordance with claim 9, further comprising a positive air pressure system configured to cool said at least one camera and configured to substantially prevent dust and dirt from entering an enclosure housing at least one of said at least one camera and said plurality of mirrors.

14. A method for inspecting a wire segment, the method comprising:
   inserting the wire segment into a mirror assembly, the mirror assembly including an odd number of sides greater than two arranged to form a pyramid structure that surrounds the wire segment, wherein a plurality of the sides include a mirror;
   wherein each mirror is sized to occupy less than half of a surface of an associated side;
   illuminating the wire segment using a light source; and acquiring a plurality of images of the wire segment that are reflected by the plurality of mirrors, wherein each image of the plurality of images shows a different side of the wire segment.

15. A method for inspecting a wire segment in accordance with claim 14, wherein inserting the wire segment into a mirror assembly comprises inserting the wire assembly into a mirror assembly having five sides.

16. A method for inspecting a wire segment in accordance with claim 14, wherein acquiring a plurality of images comprises acquiring a plurality of images using a single high-resolution camera.

17. A method for inspecting a wire segment in accordance with claim 14, wherein acquiring a plurality of images comprises acquiring a plurality of images using a plurality of digital microscopes.

18. A wire inspection system in accordance with claim 1, wherein each mirror is positioned to avoid viewing any other mirror of the mirror assembly.

\* \* \* \* \*